United States Patent [19]

Sutton et al.

[11] Patent Number: 5,308,749
[45] Date of Patent: May 3, 1994

[54] METHOD OF PREPARING BIOLOGICALLY ACTIVE REAGENTS FROM SUCCINIMIDE-CONTAINING POLYMERS, ANALYTICAL ELEMENT AND METHODS OF USE

[75] Inventors: Richard C. Sutton, Rochester; Ignazio S. Ponticello, Pittsford; Susan J. Danielson; Marsha D. B. Oenick, both of Rochester, all of N.Y.

[73] Assignee: Eastman Kodak Company, Rochester, N.Y.

[21] Appl. No.: 646,303

[22] Filed: Jan. 25, 1991

[51] Int. Cl.⁵ ................ G01N 33/531; G01N 33/543; G01N 33/546
[52] U.S. Cl. ......................................... 435/5; 422/56; 422/57; 428/403; 428/407; 436/170; 436/528; 436/531; 436/533; 436/534; 436/536; 436/538; 436/541; 524/548; 524/900; 525/279
[58] Field of Search ................ 435/5; 436/528, 531, 436/533, 534, 536, 538, 541, 170; 422/57, 56; 524/548, 900; 428/403, 407; 525/279

[56] References Cited

U.S. PATENT DOCUMENTS

| | | | |
|---|---|---|---|
| 3,857,931 | 12/1974 | Hager | 424/12 |
| 4,138,383 | 2/1979 | Rembaum et al. | 260/29.7 |
| 4,181,636 | 1/1980 | Fischer | 260/8 |
| 4,264,766 | 4/1981 | Fischer | 536/51 |
| 4,278,651 | 7/1981 | Hales | 424/1 |
| 4,323,644 | 4/1982 | Nakamura et al. | 430/518 |
| 4,451,569 | 5/1984 | Kobayashi et al. | 435/188 |
| 4,710,525 | 12/1987 | Kraemer et al. | 523/201 |
| 4,855,219 | 8/1989 | Bagchi et al. | 430/496 |
| 4,921,654 | 5/1990 | Hou et al. | 264/45.5 |
| 4,997,772 | 3/1991 | Sutton et al. | 436/533 |
| 5,030,697 | 7/1991 | Hugl et al. | 525/326.9 |
| 5,043,062 | 8/1991 | Bale et al. | 210/502.1 |

FOREIGN PATENT DOCUMENTS 8035126 6/1981 United Kingdom .

*Primary Examiner*—David Saunders
*Assistant Examiner*—Christopher L. Chin
*Attorney, Agent, or Firm*—Betty Joy James

[57] ABSTRACT

Biologically active reagents are prepared from particles of copolymers having highly active succinimid groups. The reagents are prepared by covalently attaching biologically active substances, for example antibodies, to the particles, directly or indirectly through amide groups by displacement of highly active succinimid groups on the particle surface. These reagents are used to advantage in analytical elements, methods for the detection of specific binding ligands (such as immunological species) and immunoassays, and in purification methods such as affinity chromatography.

11 Claims, No Drawings

METHOD OF PREPARING BIOLOGICALLY ACTIVE REAGENTS FROM SUCCINIMIDE-CONTAINING POLYMERS, ANALYTICAL ELEMENT AND METHODS OF USE

RELATED APPLICATION

Reference is made to copending and commonly assigned U.S. Ser. No. 07/646,132, filed on even date herewith by Sutton, Ponticello, Danielson and Oenick, and entitled "Succinimide Containing Monomers and Polymers and Latices Prepared from Same", now U.S. Pat. No. 5,200,462.

FIELD OF THE INVENTION

The present invention relates to a method of preparing biologically active reagents which uses polymeric particles. It also relates to analytical elements containing such biologically active reagents, and to immunoassays and specific binding analytical methods using them. Further, it relates to an analytical purification method using the reagents. This invention can be used for various clinical, diagnostic, medical and research purposes.

BACKGROUND OF THE INVENTION

There is a continuing need in medical practice and research, and in analytical and diagnostic procedures for rapid and accurate determinations of chemical and biological substances which are present in various fluids, such as biological fluids. For example, the presence of drugs, narcotics, hormones, steroids, polypeptides, metabolites, toxins, viruses, microorganisms or nucleic acids in human or animal body fluids or tissues must be determined rapidly and accurately for effective research, diagnosis or treatment.

A wide variety of analytical methods have been developed to detect the substances noted above. Generally, the state of the art has advanced to such a degree that analytical and diagnostic methods have become highly reliable and suitable for automation or for use with test kits which can be readily used in doctors' offices or at home. Most of such methods rely on what are known in the art as "specific binding" reactions in which an unknown substance to be detected (known as a "ligand") reacts specifically and preferentially with a corresponding "receptor" molecule. Most well known specific binding reactions occur between immunoreactants, such as antibodies and antigens (foreign substances which produce immunological responses), but other specific binding reactions (such as between avidin and biotin and a sugar with a lectin) are well known.

Methods in the art using specific binding reactions generally require that one or more or both of the reactants be immobilized on a solid substrate of some type, so that unreacted (and generally water-soluble) materials can then be separated from the water-insoluble reaction product (often called a "complex"). In addition, such immobilized reactants can be used in affinity chromatography to remove a desired biologically active material from a mixture of such materials.

U.S. Pat. No. 4,278,651 (issued Jul. 14, 1981 to Hales) relates to a supported receptor for use in an assay for a ligand in which the solid support contains a water insoluble polymer having available at least one active functional group which is either carboxyl, isothiocyanate, N-hydroxysuccinimid, imidazolide, bromoacetyl, maleimide or diazomethylene. The receptor having been covalently linked to the support through the active functional group. Generally, the support is a large core-shell particle having an outer porous coating as the shell which also has the necessary functional groups. The core of the particle provides structural integrity for the porous shell materials.

It would be expected that porous particles would provide greater surface area over non-porous particles. This, in practice, is not the case. Depending on the size of the pores, porous particles are relatively inefficient for use with large molecules of biological interest. For example, a useful ligand may be attached to a porous bead in one of the pores. The biological species which it is desired to eliminate or separate from the liquid stream may be so large as not to be able to get down into the pores and reach the ligand. Conversely, immobilization of a large affinity ligand can only take advantage of a small portion of the total surface area since the ligand itself cannot penetrate the porous well. Thus, the efficiency of binding is diminished and the apparent surface area advantage of such porous particles becomes illusory.

Acrylic acid-based photopolymerizable compositions have been prepared which are capable of binding bioactive substances after being photopolymerized, as described in U.S. Pat. No. 4,451,569 (issued May 29, 1984 to Schneider et al). These compositions may be applied as a coating on a carrier substrate, photopolymerized and a bioactive substance fixed thereto. The composition contains acrylic acid, a photoinitiator, a photopolymerization activator and adhesion promoter, and a copolymerizable olefinic monomer which contains a active functional group capable of binding bioactive substances. The olefinic monomer is preferably N-hydroxysuccinimidacrylate, N-hydroxysuccinimid amidocaproate, epoxypropyl acrylate or 2-isocyanatoethyl acrylate.

Also, biologically active substances have thus been immobilized to advantage on particulate substrates such as polymeric particles, animal and human erythrocytes, bacterial cells and other materials known in the art. In some cases, the particulate substrates are fashioned or chemically treated to provide active groups on their outer surfaces for appropriate reaction with the biological substance. If the particulate substrate is a polymeric material, it often can be prepared from monomers having the appropriate active groups.

For example, carboxylated latex particles have been used to prepare diagnostic reagents, as noted in U.S. Pat. No. 4,181,636 (issued Jan. 1, 1980 to Fischer). The described particles are prepared using a carboxyl-containing monomer such as acrylic acid, methacrylic acid, itaconic acid, aconitic acid, fumaric acid or maleic acid. Similar particles are described in U.S. Pat. No. 3,857,931 (issued Dec. 31, 1974 to Hager), U.S. Pat. No. 4,138,383 (issued Feb. 6, 1979 to Rembaum et al) and U.S. Pat. No. 4,264,766 (issued Apr. 28, 1981 to Fischer).

For example, U.S. Pat. No. 4,710,525 (issued Dec. 1, 1987 to Kraemer) relates to certain polymer particles dispersible to form a latex, to latices of such polymer particles, and to methods for immobilizing (i.e., bonding or fixing) a biologically active substance on such particles. These particles have a core-shell construction and comprise groups in the shell region which are suitable for covalent fixation thereto of a biologically active substance. The shell construction is also hydrophilic and crosslinked. The crosslinking is necessary to prevent dissolution of the very hydrophilic shell polymer. The crosslinked hydrophilic matrix of Kraemer has the disadvantage of being nonabsorptive towards antibodies and other proteins to be adsorbed or immobilized on the surface of the antibody or protein. A material that adsorbs to a hydrophilic surface can be more easily displaced than if it were adsorbed to a more hydrophobic surface.

Two known monomers, N-acryloyloxysuccinimid and N-(6-methacrylamidohexanoyloxy)succinimid, have been polymerized to form polymers. These monomers are generally water-insoluble, but are difficult to copolymerize with oleophilic monomers by emulsion polymerization in water and are not readily polymerized to form monodisperse particles.

Notwithstanding the current status of the arts of medical practice and analytical and diagnostic procedures, there is a need in the industry for a method of preparing biologically active reagents having water-insoluble, non-porous particles of a non-crosslinked copolymer useful in this invention.

SUMMARY OF THE INVENTION

The problems noted above are overcome with a method of preparing biologically active reagent comprising the step of reacting:

(I) a water-insoluble, nonporous particle of a non-crosslinked copolymer having recurring units derived from:
  (a) from 0 to about 99.9 mole percent of one or more ethylenically unsaturated polymerizable oleophilic monomers which provide hydrophobicity to a copolymer, provided that none of the monomers are crosslinking monomers,
  (b) from about 0.1 to 100 mole percent of one or more ethylenically unsaturated polymerizable monomers having a succinimidoxycarbonyl group, and
  (c) from 0 to about 10 mole percent of one or more other hydrophilic ethylenically unsaturated polymerizable monomers, with (II) a biologically active substance having been covalently attached to a particle through an amide group by displacement of the succinimidoxy portion of said succinimidoxycarbonyl group.

This invention also provides an analytical element comprising a fluid-permeable substrate having one or more reaction zones therein, and containing in at least one of the zones, a biologically active reagent as described above.

Moreover, this invention provides an analytical element comprising a nonporous support, having imposed thereon, in order and in fluid contact, a reagent layer containing one or more reagents for providing a detectable signal in the assay in response to an enzyme, a water-soluble layer containing an analog of a ligand labeled with the enzyme, and a porous spreading layer containing a biologically active reagent comprising:
  (I) the particle as described above, and
  (II) a receptor for the ligand having been covalently attached to the particle through an amide group by displacement of the succinimidoxy portion of a succinimidoxycarbonyl group.

Further, this invention provides a method for the determination of a specific binding ligand comprising:

A. contacting a specimen suspected of containing a water-soluble specific binding ligand with the reagent as described above,
to form a water-insoluble specific binding complex of the ligand with the receptor, and B. detecting the presence of the complex as an indication of the presence or absence of the ligand in the specimen.

Even further, this invention provides a method for the determination of a specific binding ligand comprising:

A. contacting a specimen suspected of containing a water-soluble specific binding ligand with the reagent as described above,
  (I) the particle as described above, and
  (II) molecules of the ligand having been covalently attached to the particle through an amide group by displacement of the succinimidoxy portion of a succinimidoxycarbonyl group, B. prior to, simultaneously with or subsequent to the contact in step A, contacting the specimen with a receptor for the ligand to form a water-soluble specific binding complex of the receptor with the water-soluble ligand and a water-insoluble specific binding complex of the receptor with the water-insoluble ligand, C. separating the water-insoluble complex from water-soluble materials, and D. detecting the presence of the water-insoluble complex as an indication of the presence or absence of the ligand in the specimen.

Also, this invention provides a method for the determination of an immunological species comprising:

A. contacting a specimen suspected of containing an immunological species with a reagent comprising:
  (I) the particle as described above, and
  (II) a receptor for the species having been covalently attached to the particle through an amide group by displacement of the succinimidoxy portion of a succinimidoxycarbonyl group,
to form a water-insoluble immunological complex of the species with the receptor, B. removing water-soluble materials from the complex, and C. detecting the presence of the complex as an indicator of the presence or absence of the immunological species in the specimen.

This invention further provides an analytical purification method comprising:

A. passing a specimen containing a mixture of biologically active substances over an affinity chromatography reagent comprising:
  (I) the particle as described above, and
  (II) a specific binding substance having been covalently attached to the particle through an amide group by displacement of the succinimidoxy portion of a succinimidoxycarbonyl group, the specific binding substance being specific to one or more predetermined biologically active substances in the specimen mixture of biologically active substances, and B. collecting the one or more predetermined biologically active substances on the reagent.

The present invention provides reagents which are useful in a variety of analytical, diagnostic and purification methods.

The advantages of the present invention are that the use of certain copolymers having a succinimid group are more easily and more completely incorporated into water-insoluble latex particles, and thereby more easily facilitate attachment of proteins or other biological compounds. Moreover, the copolymers useful in this invention have the following advantages: (1) water-insolubility, (2) they do not swell in water, (3) they are colloidally stable to the biological chemistries of immobilization, (4) they are surfactant-free, (5) they are polymer protective colloid-free, (6) they are non-porous, (7) they are non-crosslinking, and (8) they monodisperse.

Detailed Description of the Invention

The copolymers useful in the method of this invention are described in detail in U.S. Ser. No. 07/646,132 of Sutton, et al (noted above). The following discussion is provided as a summary of these copolymers.

The copolymers have essential recurring units derived from:

(a) from 0 to about 99.9 preferably from 80.0 to about 99.9, more preferably from 90.0 to about 99.9, and most preferably from 95.0 to about 99.9, mole percent of one or more ethylenically unsaturated polymerizable oleophilic monomers which provide hydrophobicity to said copolymer, provided that none of the monomers are crosslinking monomers, that is, monomers having 2 or more addition polymerizable vinyl groups capable of polymerizing to form a 3-dimensional, crosslinked polymer network, (b) from about 0.1 to 100, preferably from 0.1 to about 20 to, more preferably from 0.1 to about 10, and most preferably from 0.1 to about 5.0, mole percent of one or more ethylenically unsaturated polymerizable monomers having a succinimidoxycarbonyl group, and (c) from 0 to about 10, preferably from 0 to about 5, and more preferably from 0 to about 3, mole percent of one or more other non-crosslinking ethylenically unsaturated polymerizable monomers, such as ionic or polar hydrophilic monomers.

Preferably, the copolymer comprises monomer (b), as described above, which is represented by the structure:

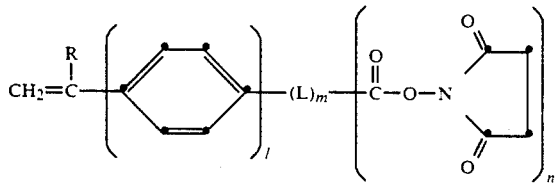

wherein:

R is hydrogen, alkyl of 1 to 3 carbon atoms or halo,

L is a linking group having at least 2 carbon atoms in the linking chain, and consisting of a combination of at least two of alkylene, having 1 to 8 carbon atoms, arylene, having about 6 to 12 carbon atoms, hetero atoms, and heteroatom-containing groups, m is 0 or 1, n is 1 or 2, and l is 0 or 1, with the proviso that when n is 2, one of the alkylene and arylene is necessarily trivalent.

More specifically, in the structure noted above, R is hydrogen, alkyl of 1 to 3 carbon atoms (such as methyl, ethyl, isopropyl and n-propyl), or halo (such as chloro or bromo). Preferably, R is hydrogen, methyl or chloro. More preferably, R is hydrogen or methyl.

Also, L is an organic linking group having at least 2 carbon atoms in the linking chain and is a combination of at least two of (1) alkylene groups having 1 to 8 carbon atoms, such as methylene, ethylene, trimethylene, propylene, pentamethylene, or 2,2-dimethyl-1,3-propylene, (2) arylene groups having 6 to 12 carbon atoms, such as phenylene, tolyene, xylylene, naphthylene, and (3) divalent hetero atoms, such as oxygen (oxy), and sulfur (thio) atoms, or (4) heteroatom-containing groups, such as carbonyl, sulfonyl, imino, (—NR$^1$ where R is hydrogen or lower alkyl of 1 or 6 carbon atoms, such as methyl, ethyl, propyl, butyl, pentyl and hexyl).

The alkylene groups can have from 1 to 8 carbon atoms, and can be branched, linear or cyclical, substituted or unsubstituted with one or more alkyl groups (preferably of from 1 to 8 carbon atoms, such as methyl, ethyl, isopropyl, hexyl and octyl), alkoxy (preferably from 1 to 12 carbon atoms, such as methoxy, ethoxy, propoxy, t-butoxy and octyloxy), cycloalkyl (preferably from 4 to 6 carbon atoms, such as cyclobutyl, cyclohexyl and cyclopentyl), aryl (preferably from 6 to 12 carbon atoms, such as phenyl, tolyl, xylyl, naphthyl, 4-methoxyphenyl and chlorophenyl). Such groups are not difficult to design or synthesize for one skilled in synthetic chemistry. The arylene groups can have from about 6 to 12 nuclear carbon atoms and can have substituents as defined for the alkylene groups.

Preferably, L comprises alkyleneoxycarbonylalkylene, alkylenethioalkyleneoxycarbonylalkylene, alkyleneiminocarbonylalkylene, iminoalkyleneoxycarbonylalkylene, alkylenethioalkylene, alkylenethioalkyleneiminocarbonylalkyleneoxyalkylene, alkylenethioalkylidyne, alkylenethioalkyleneiminocarbonylalkylenethioalkylene, alkylenethioalkyleneiminocarbonylalkylene, alkylenethioarylene, alkylenethioalkyleneoxyalkylenethioalkyleneoxycarbonylalkylene, alkyleneoxyarylenealkylenethioalkylene, alkylenethioalkyleneoxyalkylenethoalkyleneoxycarbonylalkylene, alkyleneoxyrylenealkylenethioarylenealkylenethioalkylene, alkylenethioalkyleneoxyalkylenethioalkyleneoxycarbonylarylene, carbonyloxyalkyleneoxycarbonylalkylene, carbonyloxyalkyleneureylenealkylene, carbonyloxyalkyleneiminocarbonylalkylene, or carbonyloxyalkyleneoxycarbonylalkylene.

More preferably, l is 1 and L is alkylenethioalkylene, alkylenethiophenylene, or alkylenethiophenylidyne.

Representative L groups include, but are not limited to: methyleneoxycarbonyltrimethylene, methylenethioethyleneoxycarbonyltrimethylene, methyleneiminocarbonyltrimethylene, methylene-N-methyliminoethyleneoxycarbonyltrimethylene, methylenethioethylene, methylenethioethyleneiminocarbonylmethyleneoxymethylene, methylenethio-1,1,2-ethylidynemethylenethioethyleneiminocarbonylmethylenethiomethylene, methylenethioethyleneiminocarbonyltrimethylene, methylenethio-1-carboxyethylene, methylenethiophenylene, methylenethioethyleneoxyethylenethiomethyleneoxycarbonylethylene, methyleneoxyphenylenemethylenethioethylene, methylenethioethyleneoxyethylenethioethyleneoxycarbonylethylene, methyleneoxyphenylenemethylenethiophenylenemethylenethiotrimethylene and methylenethioethyleneoxyethylenethioethyleneoxycarbonylphenylene.

Also, m is 0 or 1, n is 1 or 2, and l is 0 or 1, with the proviso that when n is 2, one of said alkylene and arylene is necessarily trivalent.

Most preferably, l and m are 0.

Preferably, monomer (b) is styrene or a styrene derivative, or an acrylic or methacrylic acid ester. More preferably, it is N-acryloyloxysuccinimide, 4-(2-succinimidoxycarbonylethylthiomethyl)styrene, 4-[1,2-bis(succinimidoxycarbonyl)ethylthiomethyl]styrene, or 4-(2-succinimidoxycarbonylphenylthiomethyl)styrene.

While the monomers (b) described above can be polymerized to form homopolymers, preferably they are used to prepare copolymers with one or more additional ethylenically unsaturated polymerizable monomers. For instance, the oleophilic monomers identified above as (a) monomers are useful for providing hydrophobicity or water-insoluble properties to the resulting copolymer. A mixture of such monomers can be used if desired. Monomers from which (a) can be derived include, but are not limited to, vinyl aromatics (for example, styrene and styrene derivatives such as 4-vinyltoluene, α-methylstyrene, 2,5-dimethylstyrene, 4-t-butylstyrene and 2-chlorostyrene), acrylic and methacrylic acid esters and amides (for example, methyl acrylate, methyl methacrylate, n-butyl acrylate, 2-ethylhexyl methacrylate, benzyl acrylate and N-phenylacrylamide), butadiene, acrylonitrile, vinyl acetate, vinylbenzyl acetate, vinyl bromide, vinylidene chloride and others readily apparent to one skilled in the art. Preferred (a) monomers are the vinyl aromatics with styrene being most preferred.

In addition, ethylenically unsaturated polymerizable monomers (c) other than those described above for monomers (a) or (b) can be copolymerized to provide desirable properties. For example, such monomers include anionic monomers containing sulfonic acid groups or salts thereof, including 2-acrylamido-2-methylpropane sulfonic acid, 3-methacryloyloxypropane-1-sulfonic acid, p-styrenesulfonic acid and salts thereof, and others readily apparent to one skilled in the art. Also included in the (c) group of monomers are nonionic hydrophilic monomers such as acrylamide, methacrylamide, N-isopropylacrylamide, 2-hydroxyethyl acrylate, 2-hydroxyethyl methacrylate, pentaethylene glycol monomethacrylate, N-vinyl-2-pyrrolidone and others readily apparent to one skilled in the art. In addition, monomers having active methylene groups, such as 2-acetoacetoxyethyl methacrylate could be used, as well as many others too numerous to mention here. A skilled polymer chemist would be able to readily fashion useful polymers from hundreds of available or producible monomers using the teaching present herein.

The copolymers of this invention are water insoluble and are readily formed as particles. The preferred monomers useful in the method of making the copolymers of this invention polymerize readily with styrene. Styrene has a low solubility in water.

The copolymers of this invention are prepared using standard emulsion or suspension polymerization techniques, as described for example by Sorenson et al in *Preparative Methods of Polymer Science*, 2nd Ed. (1968), Wiley and Sons, New York, and Stevens, *Polymer Chemistry, An Introduction*, Addison Wesley Publishing Co., London, 1975, and certain preferred conditions are discussed in copending U.S. Pat. No. 07/646,132 of Sutton et al (noted above).

During polymerization, poragens (pore-producing substance) or inert diluents are not used. If used, they would normally result in the formation of pores. If porosity was required and pore integrity is to be maintained, the particles are typically crosslinked so that they do not dissolve in the polymerization solvent or the inert diluent or poragen. Therefore, the particles of this invention are non-porous and do not require a crosslinked structure to be useful.

The copolymers described herein are critically used in particulate form in order to prepare the reagents of this invention. The average particle size can vary greatly depending upon reagent use. Generally, it is from about 0.01 to about 20 μm, preferably from about 0.01 to about 10 μm, and more preferably from about 0.05 to about 5 μm.

The reagents prepared by the method of this invention have one or more biologically active substances having been covalently attached to the polymeric particles through amide groups by displacement of the active succinimid ester groups on the outer surface of the particles. As used herein, the term "biologically active substance" is meant to include any organic compound which is found in a living organism on which is useful in the diagnosis, treatment or genetic engineering of cellular material or living organisms, and which has a capacity for interaction with another biological or chemical material. Such substances may or may not be naturally occurring in biological fluids. Such materials must be capable of attachment to the particles by displacement of the active succinimidoxy groups. Thus, generally, this means that the biologically active substance has an available amino or sulfhydryl group for reaction.

Depending upon the intended use of the reagent, the biologically active substances include, but are not limited to, amino acids, peptides, polypeptides, proteins (including antibodies, C-active protein and avidin and its derivatives), lipoproteins, glycoproteins, hormones, drugs (for example digoxin, phenytoin, phenobarbital, thyroxine, triiodothyronine, gentamicin, carbamazepine and theophylline), steroids, vitamins, polysaccharides, glycolipids, alkaloids, microorganisms, viruses, protozoa, fungi, parasites, rickettsia, molds, blood components, tissue and organ components, pharmaceuticals, haptens, lectins, toxins, nucleic acids (including oligonucleotides, either single- and double-stranded), antigenic materials (including proteins and carbohydrates), avidin or derivatives thereof, biotin or derivatives thereof, and components of any of the materials just listed, and others known to one skilled in the art.

Particularly useful reagents prepared by the method of this invention are those in which the biologically active substance is a receptor molecule specific to a ligand of interest. Thus, a specific binding reaction involving the reagent can be used for various methods (described in more detail below). Examples of ligand-receptor complexes (that is, reaction products of the ligand and receptor) include, but are not limited to antibody-antigen, antibody-hapten, avidin-biotin, sugar-lectin, gelatin-fibronectin and Protein A-IgG complexes. For purposes of this invention, complementary nucleic acids (that is, a hybridized product of complementary strands) are also considered specific binding materials. Such complementary nucleic acids (including oligonucleotides having at least 2 bases) need not be complementary at every base pair, nor must there be a matching base at every position in the nucleic acid sequence. That is, one of the strands can be longer than the other, or one strand can have a plurality of oligonucleotides complementary thereto at different sequences.

Most useful biologically active substances are what are known in the art as immunoactive species which include: (1) any substance which, when presented to an immunocompetent host, will result in the production of a specific antibody capable of binding with that substance, or (2) the antibody so produced, which compound participates in an immunological reaction. Thus, the immunological species can be an antigenic material or an antibody (including anti-antibodies and auto-antibodies). Both monoclonal and polyclonal antibodies are useful, and they can be whole molecules or various fragments thereof, as long as they have at least one active site for reaction with the active succinimidoxycarbonyl groups on the particles.

Particularly useful biologically active substances include antibodies directed to Streptococcus A, HIV-I, a microorganism associated with periodontal disease, carbamazepine, thyroxine, human chorionic gonadotropin, phenobarbital, phenytoin, digoxin or a C-active protein.

In certain embodiments, the immunological species is an enzyme which has a active group for attachment. Representative enzymes include, but are not limited to, horseradish peroxidase, glucose oxidase, urease, β-galactosidase, aspartate aminotransaminase, alanine aminotransaminase, lactate dehydrogenase, creatine phosphokinase, Y-glutamyl transferase, alkaline phosphatase, acid phosphatase and prostatic acid phosphatase.

In other embodiments, such as for competitive binding assays for determination of drugs or pregnancy, the biologically active substance is an antibody directed to human chorionic gonadotropin, phenobarbital, phenytoin or digoxin.

If desired, the biologically active substance can be modified or chemically altered to provide active groups for attaching, including providing a linking moiety for attachment. There is considerable technology known in the art for such chemical modification or the use of linking moieties, including teaching in such references as U.S. Pat. No. 4,914,210 (issued Apr. 3, 1990 to Levenson et al) and WO-A-89/2932 (published Apr. 6, 1989), both directed to modification of oligonucleotides, U.S. Pat. No. 4,719,182 (issued Jan. 12, 1988 to Burdick et al), Erlanger et al, *J. Biol. Chem.*, 234, 1090 (1959), Wiston et al, *Biochim. Biophys. Acta*, 612, pp. 40–49 (1980) and Borzini et al, *J. Immunol. Methods*, 44, pp. 323–332 (1981).

The procedure for attaching a biologically active substance to polymeric particles to prepare the reagents of this invention is generally as follows.

An aqueous suspension of the polymer particles is directly treated with a buffered solution or suspension of the biologically active material to be having been covalently bound to the polymer particles in a weight ratio of biologically active substance to polymer of about 0.1:1000 to about 1:1, preferably from about 1.0:1000 to about 100:1000, and a pH ranging from about 7.0 to about 10.0, preferably from about 8.5 to about 9.5. The mixture is mixed for a time sufficient for reaction completion, that is, as much as several hours, although from 2 to 28 hours is generally suitable. If necessary, the reactions are quenched with bovine serum albumin (BSA), then the particulates isolated (preferably by centrifugation), and resuspended in buffered saline. The isolation and resuspension steps are repeated one or more times and the final dispersion is prepared at about 0.1 to 40, and preferably 1 to 10 weight percent solids and stabilized (preferably with about 0.02% merthiolate). One skilled in the art can vary this procedure considerably, particularly the times, temperature, buffers, stabilizers, or other reagents, isolation or quenching techniques with equivalent results.

In the reaction mixture, the % solids of particles is generally from about 0.01 to about 40%, and preferably from about 1.0 to about 10%, in preparing the reagent. The amount of biologically active substance is generally designated by a weight ratio of substance to copolymer of from about 0.1:1000 to about 1:1, and preferably from about 1.0:1000 to about 100:1000. However, it should be understood that not all of the substance may become having been covalently bound to the particles. In fact, a minor amount may be adsorbed, and some may not be bound at all. One skilled in the art could readily perform tests to determine the amount of substance bound to the particles. Hence, usually an excess of substance is mixed with the particles than actually becomes covalently bound.

Mixing of the biologically active substance and particles is carried out at a temperature of from about 5 to about 50° C. preferably 18° C. to 40° C., for from about 2 to about 28 hours, preferably 4 to 24 hours. The length of time will vary with the temperature, biologically active substance and the desired coverage. Any suitable buffer can be used, but 4-(2-hydroxyethyl)-1-piperazinopropanesulfonic acid is preferred.

The details of representative procedures for making various reagents are shown in the Examples below.

The nucleic acid reagents are advantageously prepared similar to the other reagents described above, but more particularly, the polymeric particles having an average particle size of from about 0.01 to about 10 μm are present in the suspension in an amount of at least about 1% solids, and preferably from about 5% to about 25% solids. The advantage of this feature is that is produces a reagent that gives a much higher signal in an assay for cytomegaloviral DNA.

Generally, the method of preparing the nucleic acid reagents comprises:

(A) contacting (1) an aqueous suspension of succinimid-containing polymeric particles having an average particle size of 0.05 to about 10 μm, the particles being present therein at least about 1% solids with an oligonucleotide having an active amine or sulfhydryl group which reacts with the succinimidoxycarbonyl active groups to form a covalent linkage between the particles and the oligonucleotide.

Where the oligonucleotide does not have the requisite active amine or sulfhydryl groups, they can be added using known procedures and reactants as described, for example, in U.S. Pat. No. 4,914,210 (issued Apr. 3, 1990 to Levenson et al.).

In the analytical or diagnostic methods of this invention, the reagents can be used to detect any specific binding ligand for which there is a receptor molecule. The biologically active substance in a reagent of this invention can be specifically active with either the ligand or its receptor. Ligand detection can be carried out in solution or dry form (described below) using test specimens of aqueous fluids (such as biological fluids), or solutions of tissue or cellular materials, and can be quantitative, qualitative or both. In particular, the invention can be used to assay biological fluids of animals, humans or plants, but preferably fluids of humans including whole blood, sera, plasma, lymph, bile, urine, spinal fluid, sputum, lacrimal fluid, perspiration, swab specimens, tissue cultures, stool secretions, cellular fluids, vaginal secretions and semen. It is also possible to assay fluid preparations of human or animal tissue such as skeletal muscle, heart, kidney, lungs, brains, bone marrow or skin.

The ligand can be a drug, hapten, hormone, an antigenic material (lipopolysaccharide or protein) or antibody which has one or more sites for complexation with one or more of the same or different receptor molecules. In immunoassays of this invention, the ligand can be a drug (such as digoxin, phenytoin and carbamazepine), a hormone (such as thyroid stimulating hormone, human chorionic gonadotropin, leutinizing hormone and thyroxine), retroviral component or an antibody to the retrovirus (such as an HIV-I component or its antibody), bacterial infectious agents or components thereof or antibodies thereto (such as Streptococcus A antigen, Chlamydial or Gonococcal antigen or antibody), viruses or components thereof (such as hepatitis, cytomegalovirus or herpes antigen) or antibodies thereto, cancer-producing agents, or C-active protein. The ligand can also be biotin or a derivative thereof, and the receptor is avidin or a derivative thereof.

In other embodiments, the ligand can be a nucleic acid (usually in single-stranded form), the amount or presence of which is detected using a complementary single-stranded nucleic acid as the receptor molecule. There are many various assay formats for nucleic acid detection, all of which are readily apparent to one skilled in the art. Detection of HIV-I DNA, $\beta$-globin DNA or cytomegaloviral DNA is of particular interest in the practice of this invention.

In general, the method for the determination of a specific binding ligand comprises:

A. contacting a specimen suspected of containing a specific binding ligand with a reagent comprising:
   (I) a particle as described above, and
   (II) a receptor for said ligand having been covalently attached to said particle through an amide group by displacement of the succinimidoxy portion of said succinimidoxycarbonyl group, to form a water-insoluble specific binding complex of said ligand with said receptor, and B. detecting the presence of said complex as an indication of the presence or absence of said ligand in said specimen.

The ligand is preferably an antigenic material, hapten or drug. The receptor is preferably an antibody for said antigenic material, hapten or drug.

In another embodiment, the reagent can be used in competitive binding assays for determination of a water-soluble specific binding ligand. In general, such an assay comprises:

A. contacting a specimen suspected of containing a water-soluble specific binding ligand with a reagent comprising:
   (I) a particle as described above, and
   (II) molecules of the ligand having been covalently attached to the particle through an amide group by displacement of the succinimidoxy portion of the succinimidoxycarbonyl group.

B. prior to, simultaneously with or subsequent to said contact in step A, contacting said specimen with a receptor for said ligand to form a water-soluble specific binding complex of said receptor with said water-soluble ligand and a water-insoluble specific binding complex of said receptor with said water-insoluble ligand, C. separating said water-insoluble complex from water-soluble materials, and D. detecting the presence of said water-insoluble complex as an indication of the presence or absence of said ligand in said specimen.

Such competitive binding assays can be carried out in solution. A solution assay is one in which the reagents are used in a suspension of reagent and test specimen suspected of containing the ligand of interest. Either bound (that is, complexed) or unbound (that is, uncomplexed) materials can be determined in the assay. Physical separation of bound and unbound materials, if desired, can be carried out using any suitable separation technique. In using analytical elements (described below), either vertical or horizontal separation can be used. Bound ligand can be determined using light scattering, turbidimetric, radiometric or spectrophotometric techniques as are known in the art.

In a competitive binding assay, the reagent is generally present in a concentration which depends upon the amount of immunological species (that is, receptor) on the polymeric particles and the ligand of interest. A ligand analog (ligand which is detectably labeled) is also used so there is a competition between ligand and ligand analog for a known amount of receptor available for reaction. The assay is generally carried out by physically contacting and mixing the reagent, ligand analog and test specimen in a suitable container so that complexation occurs. Incubation may be used to promote complexation and any chemical or biological reactions (such as dye formation) needed for detection of the complexes.

More particularly, the ligand is an immunological species and the reaction of ligand and receptor therefor forms an immunological complex which is detectable once water-soluble (uncomplexed) materials are removed from the complex (for example, by filtration or centrifugation) to indicate the presence or absence of the species in the specimen.

The methods of this invention can also be carried out using dry analytical elements. The simplest element can be composed of an adsorbent, fluid permeable substrate, for example, a thin sheet of a self-supporting adsorbent or bibulous material such as a filter paper or paper strip. This substrate has one or more reaction zones for chemical, biological or specific binding reactions to occur therein. The reagent of this invention is present in at least one of these zones. Other optional zones can include other reagents, such as dyes, dye-providing compounds, scavengers, antioxidants, enzyme substrates or buffers and other materials readily apparent to one skilled in the art. Such elements are known in the art as test strips, analytical elements, slides or dip sticks.

Absorbent materials useful in preparing the elements can include cellulosic materials (such as porous papers), porous polymeric films, mats of glass fibers, woven or nonwoven fabrics and other materials known to one skilled in the art. Preferred substrates are porous spreading layers as described, for example, in U.S. Pat. No. 3,992,158 (issued Nov. 16, 1976 to Przybylowicz et al), U.S. Pat. No. 4,258,001 (issued Mar. 24, 1981 to Pierce et al), U.S. Pat. No. 4,292,272 (issued Sep. 29, 1981 to Kitajima et al) and U.S. Pat. No. 4,430,436 (issued Feb. 7, 1984 to Koyama et al).

Preferred elements can include one or more superposed fluid-permeable layers, all of which are superposed on a nonporous, fluid impermeable support (which can be transparent or not) composed of a suitable polymeric, cellulosic or metallic material. The layers can be used for various purposes, such as for reaction zones, subbing zones, reagent zones, barrier zones, radiation-blocking zones and other uses well known in the art. Where desired, reagents and buffers can move among the layers for the desired reactions to carry out the assay and provide a detectable product and separation of bound and unbound materials. Other components of analytical layers are described, for example, in U.S. Pat. No. 4,042,335 (issued Aug. 16, 1977 to Clément), U.S. Pat. No. 4,132,528 (issued Jan. 2, 1979 to Eikenberry et al), U.S. Pat. No. 4,144,306 (issued Mar. 13, 1979 to Figueras), U.S. Pat. No. 4,670,381 (issued Jun. 2, 1987 to Frickey et al) and EP-A-0 253 581 (published Jan. 2, 1988).

While it is preferred that the reagent of this invention be incorporated into an element for use, this is not critical because the reagent can be added to the element at the time of the assay along with the test specimen. Preferably, however, the ligand analog and reagent of this invention (containing the appropriate receptor) are located within the element in different zones so they will not complex prematurely.

This invention also provides an analytical element comprises a fluid-permeable substrate having one or more reaction zones therein, and containing in at least one of said zones, a biologically active reagent comprising:

(I) the particle as described above, and
(II) a biologically active substance having been covalently attached to the particle through an amide group by displacement of the succinimidoxy portion of a succinimidoxycarbonyl group.

In one preferred embodiment of this invention, an analytical element comprises a nonporous support, having imposed thereon, in order and in fluid contact, a reagent layer containing one or more reagents for providing a detectable signal in the assay in response to an enzyme, a water-soluble layer containing an analog of a ligand labeled with said enzyme, and a porous spreading layer containing a biologically active reagent comprising: (I) a water-insoluble, nonporous particle of a noncrosslinked copolymer as previously described herein, and (II) a receptor for the ligand having been covalently attached to the particle through an amide group by displacement of the succinimidoxy portion of a succinimidoxycarbonyl group.

Preferably, the ligand analog is labeled with an enzyme, such as one described below, the ligand is an antigenic material, hormone, hapten or drug, and the receptor is the corresponding antibody or immunoreactant. Such elements are particularly useful for the determination of carbamazepine, thyroxine, phenobarbital, phenytoin or digoxin. Most preferably, they are useful for the determination of phenobarbital, phenytoin or digoxin.

A variety of different elements, depending upon the method of assay, can be prepared according to this invention. They can be configured in a variety of forms, including elongated tapes of any desired width, sheets, slides or chips.

The solution or dry assay of this invention can be manual or automated. In general, in the use of dry elements, analyte determination is made by taking the element from a supply roll, chip packet or other source and physically contacting it with a sample of test specimen so the specimen and reagents within the element become mixed in one or more test zones. Such contact can be accomplished in any suitable manner, for example, by dipping or immersing the element into the sample or, preferably, by applying a drop of the specimen to the element with a suitable dispensing means. Wash fluids can also be used in the assay, for example as described in U.S. Pat. No. 4,517,288 (issued May 14, 1985 to Giegel et al).

Assay results are generally determined by observing detectable spectrophotometric changes in the element either visually or with suitable detection equipment.

Another embodiment of this invention is what is known in the art as agglutination assays whereby a ligand is complexed with the reagent of this invention to form a detectable agglutination or clumping of the particles. The resulting agglutination can be detected in a variety of ways, for example visually or with suitable light scattering detection equipment. Representative agglutination techniques are described, for example, in U.S. Pat. No. 4,419,453 (issued Dec. 6, 1983 to Dorman et al), U.S. Pat. No. 4,808,524 (issued Feb. 28, 1989 to Snyder et al), U.S. Pat. No. 4,828,978 (issued May 9, 1989 to Warren III et al) and U.S. Pat. No. 4,847,199 (issued Jul. 11, 1989 to Snyder et al).

Agglutination assays are preferably carried out using reagents of the present invention which are detectably labeled in some manner, such as with a radioisotope in the particle or in the biologically active substance attached thereto, or with a colorimetric or fluorometric dye associated with the particle. Most preferably, a dye is within the interior of the particle, that is away from its surface so as to not interfere with the attachment of a biologically active substance or its complexation. Such particles can be core-shell particles having the dye within a core polymer while the shell copolymer is free of dye. This feature and methods of making such particles are described in more detail in U.S. Pat. No. 4,808,524 (noted above) and in EP-A-0 280 556 (published Aug. 31, 1988). In core-shell polymer particles, the shell copolymer has a composition like that described herein (that is, having the necessary active succinimidoxycarbonyl groups), but the core polymer can be different and need not have active groups.

Also, a method for the determination of an immunological species is provided comprising:

A. contacting a specimen suspected of containing an immunological species with a reagent of this invention having a receptor for the species which is having been covalently attached to the particle through an amido group by displacement of the succinimidoxy portion of the succinimidoxycarbonyl group, to form a water-insoluble immunological complex of the species with the receptor, removing water-soluble materials from the complex preferably by filtration, and detecting the presence of the complex as an indicator of the presence or amount of the immunological species in the specimen. It is preferred that the reagent be immobilized on a microporous filtration membrane.

The immunological species can be an antigenic material and the receptor an antibody therefor. Alternatively, the immunological species can be an antibody and the receptor an antigenic material specific therefor.

The reagent of this invention can be used in immunometric assays (often called "sandwich" assays). In such assays, the ligand of interest is complexed with two or more receptor molecules (the same or different), one of which is insolubilized or capable of being insolubilized (such as through an avidin-biotin bond), and the other being water-soluble and appropriately labeled (such as with a radioisotope, enzyme, chemiluminescent moiety or other marker known in the art). For example, a sandwich assay for a ligand such as human chorionic gonadotropin (hCG) can be carried out with a reagent of this invention having antibodies to the hormone in combination with enzyme-labeled antibodies to hCG which will complex at different epitopic sites than the reagent antibodies. The resulting sandwich complex is insoluble, detectable and separatable from uncomplexed materials (such as with a microporous filtration membrane). In a preferred embodiment, the reagent of this invention has a receptor for the ligand of interest, and is immobilized on the membrane. Sandwich assays are well known in the art, including GB-A-2,074,727 (published Nov. 4, 1981) and U.S. Pat. No. 4,486,530 (issued Dec. 4, 1984 to David et al), and references noted therein.

Preferably, in the sandwich assays, either prior to, simultaneously with or subsequently to the formation of the water-insoluble complex with the reagent of this invention, the ligand of interest is reacted with a water-soluble specific binding component specifically active therefor.

Other ligands which can be detected in sandwich assays according to this invention include, but are not limited to, Streptococcal antigens, antigens extracted from microorganisms associated with periodontal diseases, hepatitis antigens, HIV-I and other retroviral antigens.

In the sandwich assay, the reagent of this invention can be directly reacted with the ligand of interest, for example, where the ligand is an antigen, and the reagent comprises antibodies thereto. Alternatively, the reagent is complexed with the ligand indirectly, that is, through an intermediate linking moiety. One example of this is shown in U.S. Pat. No. 4,870,007 (issued Sep. 26, 1989 to Smith-Lewis) where complexation is through an avidin-biotin bond.

Another embodiment of this invention is what is known as a hybridization assay wherein a targeted nucleic acid is detected using complementary probes, one of which is suitably labeled, and the other is immobilized, or capable of being immobilized. The reagent of this invention can be used as an immobilized probe (also known as a capture probe) in such assays. Examples of hybridization assays are shown, for example, in U.S. Pat. No. 4,358,535 (issued Nov. 9, 1982 to Falkow et al) and U.S. Pat. No. 4,486,539 (issued Dec. 4, 1984 to Ranki et al). These reagents can also be used as capture probes after what is known in the art as polymerase chain reaction amplification, for example, as described in more detail in U.S. Pat. No. 4,683,195 (issued Jul. 28, 1987 to Mullis et al), U.S. Pat. No. 4,683,202 (issued Jul. 28, 1987 to Mullis) and EP-A-0 370,694 (published May 30, 1990). An amplified nucleic acid is immobilized by hybridization with the reagent of this invention.

In particular, a method for the detection of a nucleic acid comprises:

A. forming a water-insoluble hybridization product between a nucleic acid of interest, with a reagent of this invention comprising an oligonucleotide having been covalently attached to the particle through the active succinimidoxycarbonyl group, the oligonucleotide being substantially complementary to the nucleic acid of interest, and B. detecting the presence of the hybridization product as an indication of the presence or amount of the nucleic acid of interest.

In preferred hybridization assays, the nucleic acid of interest is amplified using polymerase chain reaction (known in the art) with suitable reagents (for example, DNA polymerase, dNTPs, primers) prior to capture with the reagent of this invention. HIV-I DNA, cytomegaloviral DNA and $\beta$-globin DNA are readily detected using amplification and detection according to this invention. In one embodiment, one of the primers is biotinylated, and detection of the amplified nucleic acid is accomplished using a conjugate of avidin and an enzyme. The hybridized product can be captured using the reagent which may be attached to or localized on a substrate of some type, including a microporous substrate such as a membrane, or a compartment of a self-contained reaction pouch.

The analytical, sandwich and hybridization assays of this invention can be carried out using suitable equipment and procedures whereby complexed or hybridized product is captured or separated from uncomplexed materials by filtration, centrifugation or other means. Preferably, such assays are carried out using disposable test devices which contain microporous filtration membranes (for example those commercially available from Pall Corp.). Representative test devices are shown in U.S. Pat. No. 3,825,410 (issued Jul. 23, 1974 to Bagshawe), U.S. Pat. No. 3,970,429 (issued Jul. 20, 1976 to Updike) and U.S. Pat. No. 4,446,232 (issued May 1, 1984 to Liotta). Particularly useful test devices are shown in U.S. Ser. No. 98,248 (filed Sep. 18, 1987 by Hinckley et al), and are commercially available as Surecell TM test devices (Eastman Kodak Co.).

The analytical separation method of this invention can be used to isolate one or more analytes of interest from a mixture of biological materials. Thus, the reagent of this invention (or several reagents having different substances attached to particles) is generally placed in a column through which a fluid containing the mixture of biological materials is poured, allowing the reagent to extract from the fluid those materials one wants to isolate. This may be useful in the purification of nucleic acids, enzymes, carbohydrates, proteins, lipids, vitamins, steroids, antibodies, peptides or hormones. This procedure is also known as affinity chromatography.

Affinity chromatography can also be used to concentrate dilute solutions of proteins in order to remove denatured forms thereof from refined proteins, and in the separation and resolution of protein and peptide components which have originated in specific chemical modifications.

Another use of this method is to purify nucleic acids, such as those resulting from polymerase chain reaction amplification, as described, for example in EP-A-O 388,171 (published Sep. 19, 1990).

The reagent of this invention can be supplied for any of the described methods as a single material, or it can be supplied in an analytical element as described above, or yet again in combination with other reagents, test devices and equipment in a diagnostic test kit. For the purification method, the reagent can also be supplied in an affinity chromatography column.

The analytical purification method of this invention comprises (A) passing a specimen containing a mixture of biologically active substances over an affinity chromatography reagent comprising the particles described above, and a specific binding substance having been covalently attached to said particle through an amide group by displacement of the succinimidoxy portion of the succinimidoxycarbonyl group, with the specific binding substance being specific to one or more predetermined biologically active substances in the specimen mixture of biologically active substances, and collecting the one or more predetermined biologically active substances on the reagent.

In one embodiment, the predetermined substances are captured by the reagent, the original eluent is discarded and the captured substances are removed from the column using a solvent which alters the binding characteristics of the substances so they can be uncomplexed. Such solvents include buffers which alter the pH, salt solutions which alter the ionic nature of the complex or solutions containing a second species which will specifically bind to the reagent and replace the captured substance.

Alternatively, the predetermined substances captured by the reagent are discarded, and other chemical or biological materials remaining in the original eluent are collected.

The following examples are for illustrative purposes only, and not to limit the scope of the invention. All percentages are by weight, unless otherwise specified.

EXAMPLE 1

Immobilization of anti-phenobarbital antibody Phe 1.9 on polymer beads of the invention and retention of antibody activity The following copolymer beads were evaluated:

| SAMPLE | COMPOSITION |
|---|---|
| 1 | Poly(styrene-co-N-acryloyloxysuccinimid) (Molar ratio 96.83/3.17; Weight ratio 85/5) |
| 2 | A core/shell polymer having a core of poly(styrene-co-ethylene dimethacrylate) (molar ratio 99/1) and a shell of poly(styrene-co-m- and p-(60/40)-(2-chloroethylsulfonylmethyl)styrene-co-ethylene dimethacrylate) (molar ratio 94.5/4.5/1) |
| 3 | Poly(styrene-co-m- and p-(60/40)-2-(2-chloroethylsulfonylmethyl)styrene-co-methacrylic acid) (molar ratio 89.14/4.16/6.34) |

The beads were all treated under the same condition. A reaction dispersion was prepared comprising 0.3 mg of anti-phenobarbital antibody 1.9 and 30 mg dry weight of beads in 0.1M EPPS buffer [N-(2-hydroxyethyl)piperazine-N'-(3-propane-sulfonic acid)], pH 8.5, 1.5 ml final volume and placed in tubes. The capped tubes containing the reaction mixtures were rotated end-over-end at room temperature for 4 hours. The reactions were quenched by the addition of 0.3 ml of bovine serum albumin (BSA) solution at 100 mg/l. The tubes were rotated end-over-end for an additional 16 hours at room temperature. The reaction mixtures were centrifuged, the supernatants removed, and the beads resuspended in 1 ml of PBS (phosphate buffered saline, pH 7.4). This step was repeated 3 more times. The final resuspension was in 1.8 ml PBS, and merthiolate was added to 0.02% final concentration.

Identical reactions were performed using $^{125}$I-labeled BGG (bovine gamma globulin). These reactions were performed to assess the total mass of antibody adsorbed to the surface. The analysis was performed as follows: a quantity of 0.18 ml of the reaction mixture following addition of the BSA quench was taken and monitored for radioactivity. As in the case of the Phe 1.9 beads, the beads were centrifuged; a 0.18 ml sample of the supernatant was taken and monitored for radioactivity. The remainder of the supernatant was removed and the beads were resuspended in 1 ml of PBS. The beads were centrifuged once more. The beads were resuspended in 1 ml of 1% sodium dodecyl sulfate and monitored for radioactivity. The ratio of radioactivity of the washed beads to the initial radioactivity of the reaction mixture was used to calculate the amount of $^{125}$I-BGG, and by analogy the amount of Phe 1.9 antibody, adsorbed on the bead surfaces.

The relative amounts of active antibody in the preparations were determined in an assay in which serial dilutions of the antibody bead dispersions were mixed with a fixed concentration of one of two antigens: phenobarbital-enzyme label or $^3$H-phenobarbital. The reaction between the diluted antibody bead dispersions and the enzyme labels were incubated for one hour at room temperature with constant agitation in PBS containing 0.1% BSA. Following incubation, the beads were centrifuged and a sample of the supernatant was removed to determine the concentration of antigen remaining in solution. The antibody binding sites required to bind 50% of the antigens were calculated. The results are summarized below:

| | Nanomolar theoretical binding sites required to remove 50% of the antigen | |
|---|---|---|
| Sample | enzyme-label at 5e-10M total | $^3$H-Phenobarbital at 5e-9M total |
| 1 | 0.60 | 11 |
| 2 | 1.4 | 25 |
| 3 | 1.0 | 25 |

These results show that Phe 1.9 immobilized on the beads of Sample 1 can bind more phenobarbital-enzyme conjugate or phenobarbital drug at lower concentrations of immobilized Phe 1.9 indicating that Phe 1.9 immobilized on said beads retains more activity than when immobilized on the other beads.

EXAMPLE 2

Immobilization of anti-phenytoin antibody DPH 1.2 on copolymer beads of this invention and retention of activity The following copolymer beads were evaluated.

| SAMPLE | COMPOSITION |
|---|---|
| 1 | Same polymer as in Example A, sample 1, except having a molar ratio of 87.32/12.68 rather than 96.83/3.17 |
| 2 | Same polymer as Example A, Sample 2 |
| 3 | Poly(styrene-co-m- and p-(60/40)-(2-chloroethylsulfonylmethyl)styrene-co-ethylene dimethacrylate) (molar ratio 94.5/4.5/1) |
| 4 | Poly(styrene-co-acrylic acid) (molar ratio 97.5/2.5) |
| 5 | Poly(styrene-co-m- and p-(60/40)-(4-carboxybutyryloxymethyl)styrene) (molar ratio 97.84/2.16) |
| 6 | Poly(styrene-co-4-carboxybutyryloxyethyl methacrylate) (molar ratio 97.84/2.16) |
| 7 | Poly(styrene-co-4-carboxybutyrylpoly-(oxyethylene) methacrylate (molar ratio 98.71/2.19) |

The activator for the reaction of the lysine residues of the antibody with the carboxylic acid groups of copolymers 4-7 is 1-(1-pyrrolidinylcarbonyl)pyridinium chloride (DS-1).

The beads were all treated under the same conditions. Reaction dispersions were prepared comprising 0.3 mg of antibody (anti-phenytoin antibody DPH 1.2) and 30 mg dry beads and a final volume of 1.5 ml. For beads 1-3, 0.1M EPPS buffer, pH 8.5 was used. For beads 4-7, 0.1M MES (2-(4-morpholino)ethanesulfonic acid) was used and 0.5 mmol of DS-1 activator/g beads (0.015 mmol) was present. The antibody bearing beads were prepared as follows:

Aliquots of the polymer particle dispersions containing 30 mg beads dry weight were placed in 2 ml microfuge tubes. The appropriate buffers were added to bring the volume in each tube to 1.5 ml. The beads were centrifuged 10 min. at 13,000 rpm and the supernatant discarded. Beads 1-3 were resuspended with 1.393 ml of 0.1M EPPS buffer. Beads 4-7 were resuspended with 1.093 ml of 0.1M MES buffer. A solution of DS-1 (0.3 ml of a solution at 0.05M in 0.1M MES) was added to tubes 4-7; the tubes were capped and rotated end-over-end for 10 minutes. An aliquot (0.107 ml at 2.82 mg/ml) anti-phenytoin antibody DPH 1.2 was added to each tube, the tubes were capped and rotated end-over-end for 4 hours.

The reactions were quenched by the addition of 0.3 ml of bovine serum albumin solution at 100 mg/ml. The tubes were rotated end-over-end for an additional 16 hours at room temperature. The reaction mixtures were centrifuged, the supernatants removed and saved for analysis, and the beads resuspended in 1 ml of PBS. This step was repeated 3 more times. The final resuspension was in 1.8 ml PBS and merthiolate was added to 0.02% final concentration.

The supernatants from the reaction mixture were analyzed for total antibody concentration by ELISA. The amount of antibody bound to the surface was calculated from this result.

The relative amounts of active antibody in the preparations were determined in an assay in which serial dilutions of the antibody bead dispersion were mixed with a fixed concentration of one of three different antigens: hapten-enzyme conjugates prepared with two different haptens (5,5-diphenylhydantoin-3-ω-valeric acid (DPH-val-) and 5-ethyl-5-phenylhydantoin-3-ω-valeric acid (EPH-val) and $^3$H-phenytoin. The reaction between the diluted antibody head dispersions and the various antigens were incubated for one hour at room temperature with constant agitation in PBS containing 1.0% BSA. The amount of enzyme-label or $^3$H phenytoin remaining in solution after centrifugation was determined and the theoretical number of binding sites required to bind 50% of the antigens were calculated. The results are show below:

| | Nanomolar theoretical binding sites required to bind 50% of the antigen at 5e-10M total | | |
|---|---|---|---|
| Sample | DPH-val-enzyme | EPH-val-enzyme | $^3$H-phenytoin |
| 1 | 2.5 | 2.5 | 1.2 |
| 2 | 2.5 | 4.0 | 1.2 |
| 3 | 2.0 | 5.0 | 1.1 |
| 4 | 10 | 120 | 12 |
| 5 | 15 | 120 | 6.0 |
| 6 | 10 | 80 | 6.0 |
| 7 | 25 | >250 | 15 |

These results show DPH 1.2 immobilized on beads of Sample 1 binds EPH-val-enzyme at lower concentrations of immobilized binding sites than DPH 1.2 immobilized on any of the other beads. This indicates that DPH 1.2 retains more EPH-val-enzyme binding sites when immobilized on beads of the invention than when immobilized on the other beads. DPH 1.2 retains more activity toward the antigen when immobilized on beads of Sample 1 than when immobilized on any of the carboxylic acid group bearing beads. DPH 1.2 activity toward DPH-val-enzyme and $^3$H-phenytoin when immobilized on Sample 1 beads is similar to the activity of DPH 1.2 immobilized on the type beads which have chloroethylsulfonyl groups.

EXAMPLE 3

Reaction of the Particles of Example 1, Sample 1 with $^3$H BGG

One portion of Example 1, Sample 1 (93 μL, 16.2%) solids containing 15 mg of polymer (dry weight) was combined with 27 μL at 10 mg/ml (0.273 mg) of labeled (tritiated) bovine gamma globulin ($^3$H BGG) and brought to a final volume of 1.5 ml with 0.1M EPPS, pH 8.5, in a microcentrifuge tube. [EPPS=4-(2-hydroxyethyl)-1-piperazinopropanesulfonic acid.] The reaction was continued for 24 hours at room temperature by end-over-end rotation of the tube at 30-35 rpm while attached to a rotating plate mounted at a 45° angle. A second portion was treated as described above except that the reaction was conducted at 37° C.

At the end of the described reaction times, each reaction was quenched by addition of excess BSA, bovine serum albumin (250 μL of BSA at 100 mg/ml) and continuing rotation for an additional 4 hours.

The total amount of $^3$H BGG bound was determined by measuring: a) the cpm (counts per minute) of a 250 μL aliquot of the reaction mixture; b) the cpm of a 250 ml aliquot of the supernatant following centrifugation at 14,000 rpm, 10 min, of a 1 ml sample of the reaction mixture; and c) the cpm of the material bound to the latex following repeated washes of the pellet obtained in (b). The fraction of BGG which is having been covalently bound to the latex was determined following incubation of a 500 μL reacted latex in the presence of 400 μL of 0.1M EPPS buffer and 100 μL of 10% sodium dodecyl sulfate (SDS) at 37° C. for 20 hours with end-over-end rotation. The same procedure described above for determining the total amount of $^3$H BGG bound is used to determine the amount having been covalently bound. The results are reported in Tables I and II.

TABLE I

| | BGG Bound to Polymer | | | |
|---|---|---|---|---|
| SAMPLE | REACTION TEMP. | $^3$H BGG OFFERED | % BOUND | mg BGG/g POLYMER |
| 1 | Room Temp | 0.5 mg | 82 | 2.7 |
| 2 | 37° C. | 0.5 mg | 85 | 2.8 |

TABLE II

| | $^3$H BGG Covalently Bound (After SDS Treatment) | | | |
|---|---|---|---|---|
| SAMPLE | REACTION TEMP | % BOUND | mg BGG/g POLYMER | RATIO COVALENT/ TOTAL |
| 1 | Room Temp | 57 | 1.9 | .69 |
| 2 | 37° C. | 60 | 2.0 | .71 |

The results of these reactions show that roughly equivalent amounts of ³H BGG are having been covalently attached at either temperature.

The invention has been described in detail with particular reference to certain preferred embodiments thereof, but it will be understood that variations and modifications can be effected within the spirit and scope of the invention. Moreover, all patents, patent applications (published or unpublished, foreign or domestic), literature references or other publications noted above are incorporated herein by reference for any disclosure pertinent to the practice of this invention.

We claim:

1. A method of preparing a biologically active reagent comprising the step of reacting:
   (I) a water-insoluble, nonporous particle of a noncrosslinked copolymer having recurring units derived from:
   (a) from 0 to about 99.9 mole percent of one or more ethylenically unsaturated polymerizable oleophilic monomers which provide hydrophobicity to said copolymer, provided that none of said monomers are crosslinking monomers,
   (b) from about 0.1 to 100 mole percent of one or more ethylenically unsaturated polymerizable monomers having a succinimidoxycarbonyl group, and
   (c) from 0 to about 10 mole percent of one or more other ethylenically unsaturated polymerizable monomers, with
   (II) a biologically active substance to covalently attach said biologically active substance to said particle through an amide group by displacement of the succinimidoxy portion of said succinimidoxycarbonyl group.

2. The method of claim 1 wherein said biologically active substance is an immunoactive species.

3. The method of claim 1 wherein said biologically active substance is an antibody.

4. The method of claim 1 wherein monomer (b) is represented by the structure:

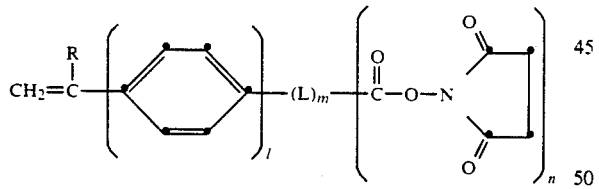

wherein:
R is hydrogen, alkyl of 1 to 3 carbon atoms or halo,
L is a linking group having at least 2 carbon atoms in the linking chain and consists of a combination of at least two of alkylene, having 1 to 8 carbon atoms, arylene, having about 6 to 12 carbon atoms, hetero atoms, or heteroatom-containing groups,
m is 0 or 1, n is 1 or 2, and l is 0 or 1, with the proviso that when n is 2, one of said alkylene and arylene is necessarily trivalent.

5. The method of claim 4 wherein R is hydrogen, methyl, or chloro.

6. The method of claim 4 wherein monomer (b) is N-acryloyloxysuccinimide, 4-(2-succinimidoxycarbonylethylthiomethyl)styrene, 4-(1,2-bis(succinimidoxycarbonyl)ethylthiomethyl)styrene, 4-(2-succinimidoxycarbonylphenylthiomethyl)styrene.

7. An analytical element comprising a fluid-permeable substrate having one or more reaction zones therein, and containing in at least one of said zones, a biologically active reagent comprising:
   (I) a water-insoluble, nonporous particle of a noncrosslinked copolymer having recurring units derived from:
   (a) from 0 to about 99.9 mole percent of one or more ethylenically unsaturated polymerizable oleophilic monomers which provide hydrophobicity to said copolymer, provided that none of said monomers are crosslinking monomers,
   (b) from about 0.1 to 100 mole percent of one or more ethylenically unsaturated polymerizable monomers having a succinimidoxycarbonyl group, and
   (c) from 0 to about 10 mole percent of one or more other ethylenically unsaturated polymerizable monomers, and
   (II) a biologically active substance having been covalently attached to said particle through an amide group by displacement of the succinimidoxy portion of said succinimidoxycarbonyl group.

8. The element of claim 7 wherein said biologically active substance is an immunoreactant.

9. The element of claim 7 wherein said biologically active substance is an antibody.

10. The element of claim 7 wherein monomer (b) is represented by the structure:

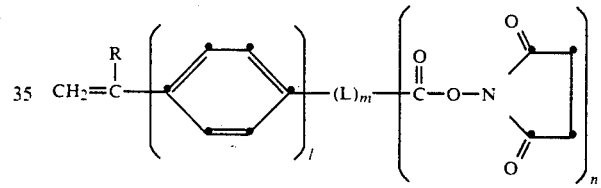

wherein:
R is hydrogen, alkyl of 1 to 3 carbon atoms or halo,
L is a linking group having at least 2 carbon atoms in the linking chain and is a combination of at least two of (1) alkylene groups having 1 to 8 carbon atoms, (2) arylene groups having about 6 to 12 carbon atoms, and (3) hetero atoms, or (4) heteroatom-containing groups,
m is 0 or 1, n is 1 or 2, and l is 0 or 1, with the proviso that when n is 2, one of said alkylene and arylene is necessarily trivalent.

11. An analytical element comprising a nonporous support, having imposed thereon, in order and in fluid contact,
a reagent layer containing one or more reagents for providing a detectable signal in response to an enzyme,
a water-soluble layer containing an analog of a ligand labeled with said enzyme, and
a porous spreading layer containing a biologically active reagent comprising:
(I) a water-insoluble, nonporous particle of a noncrosslinked copolymer having recurring units derived from:
(a) from 0 to about 99.9 mole percent of one or more ethylenically unsaturated polymerizable oleophilic monomers which provide hydrophobicity to said copolymer, provided that none of said monomers are crosslinking monomers, (b) from about 0.1 to 100 mole percent of one or more ethylenically unsaturated polymerizable monomers having a succinimidoxycarbonyl group, and (c) from 0 to about 10 mole percent of one or more other ethylenically unsaturated polymerizable monomers, and (II) a receptor specific for said ligand having been covalently attached to said particle through an amide group by displacement of the succinimidoxy portion of said succinimidoxycarbonyl group.

* * * * *